US00PP13886P3

(12) United States Plant Patent
Zipperer, III

(10) Patent No.: US PP13,886 P3
(45) Date of Patent: Jun. 17, 2003

(54) GLADIOLUS PLANT NAMED 'SIBERIA'

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 0 days.

(21) Appl. No.: 09/877,572

(22) Filed: Jun. 8, 2001

(65) Prior Publication Data

US 2002/0188987 P1 Dec. 12, 2002

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, Zipperer, III, filed Dec. 20, 2000.
U.S. patent application Ser. No. 09/742,726, Zipperer, III, filed Dec. 20, 2000.
U.S. patent application Ser. No. 09/877,571, Zipperer, III, filed Jun. 8, 2001.
U.S. patent application Ser. No. 09/877,573, Zipperer, III, filed Jun. 8, 2001.
U.S. patent application Ser. No. 09/877,574, Zipperer, III, filed Jun. 8, 2001.
U.S. patent application Ser. No. 09/877,575, Zipperer, III, filed Jun. 8, 2001.
U.S. patent application Ser. No. 09/918,662, Zipperer, III, filed Jul. 31, 2001.
U.S. patent application Ser. No. 09/918,660, Zipperer, III, filed Jul. 31, 2001.
U.S. patent application Ser. No. 09/918,663, Zipperer, III, filed Jul. 31, 2001.

*Primary Examiner*—Bruce R. Campell
*Assistant Examiner*—Anne Marie Grünberg
(74) *Attorney, Agent, or Firm*—Laura G. Barrow

(57) ABSTRACT

A new and destinct gladiolus variety, designated 'Siberia', is shown and described. Compared to the 'T-200' variety, the 'Siberia' variety is 25 cm taller and will maintain one to two more flowers in open bloom. The 'Siberia' variety is also able to maintain up to six to seven flowers in open bloom simultaneously, beginning with a tight cut stem.

2 Drawing Sheets

The present invention comprises a new and distinct variety of a Gladiolus l. referred to by the variety name 'Siberia'.

BRIEF DESCRIPTION OF THE PHOTOGRAPHS

ASEXUAL REPRODUCTION

The new variety was originated by the Application in a controlled proprietary breeding program in Ft. Myers, Fla. wherein selected gladiolus varieties were crossed. The female parent was a gladiolus variety named 'Dr. Magee,' an unpatented variety characterized in part by having a small pink bloom, a short stem having a short flower head, and high resistance to Fusarium fungi species. The male parent was a white gladiolus variety named 'T-200,' an unpatented, released variety by Turk characterized in part by having a harvesting time similar to the 'White Friendship' gladiolus variety, 16 to 18 florets, and lightweight stems. The seeds were planted in Ft. Myers, Fla., and the selection of the 'Siberia' variety was made in Spring 1988. Asexual reproduction of the 'Siberia' variety was achieved by collecting cormels from the first corm and growing said cormels to maturity in Ft. Myers, Fla. All subsequent asexual reproductions of the 'Siberia' variety remain true to the original variety type.

BOTANICAL DESCRIPTION

Figure 1:
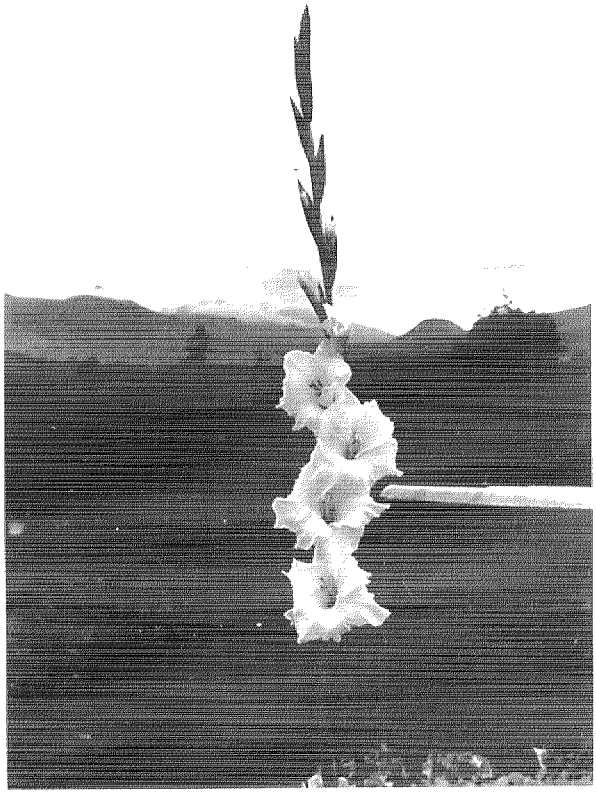
FIG. 1 is a photograph of the variety plant in bloom.
Figure 2:
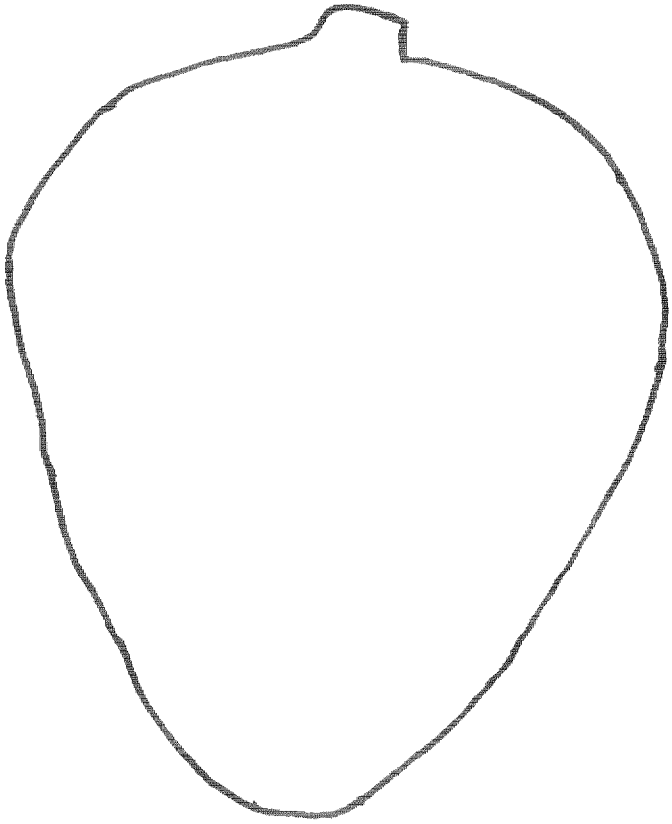
FIG. 2 is a drawing illustrating the shape and size of the large petals.

The accompanying color photograph (FIG. 1) shows the inflorescence and various stages of blooming of the 'Siberia' variety plant.

The following botanical description, except for color, of the 'Siberia' variety was observed when the plant was 75 days old grown under the following conditions in Ecuador:

(1) Twelve-hour daylight days with high light intensity;

(2) Temperatures: 58–60° F. (low's) and 69–75° F. (high's);

(3) Humidity: 50–55%

(4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to the R.H.S. Colour Chart were made in the Netherlands under similar environmental conditions as described above, but at increased day lengths of 12 to 17 hours and 50% to 65% humidity.

The spike of the plant is about 122 cm and comprises 17 florets when grown from #2 size corms (1.25–1.50 inches) in Ecuador. The color of the stem is Yellow Green Group 144B. The head length is about 49 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes).

The leaf color of the 'Siberia' variety is Green Group 137C. The leaf size is about 74 cm (length) by 3 cm (width).

The bud size of the 'Siberia' variety is about 6 cm in length. The bloom consists of three large petals on the back, two medium petals on the top half of the bloom, and one small petal on the bloom half of the bloom. The petals are distinctively arranged such that the medium and small petals form an inverse triangle with respect to the large petals. The color of the corolla bloom is a pure white. Specifically, the tight bloom is Green White Group 157A. The bloom in open perfect condition is White Group N155D. The bloom open going down is White Group N155C. The color of the bloom deep in the throat is Yellow Green Group 145C. Red dots (Red Purple Group 70B) distributed within the throat are also observed. The diameter of the entire bloom is about 13 cm.

The variety has three stamens and one pistil. The color of the pistil head is Purple Group 77B. The color of the pistil stem is White Group N155B. The color of both the stamen head and stamen stem is White Group N155D.

The corms of the 'Siberia' variety are typical for the gladiolus and have a Yellow Group 13B color under the husk on the top of the bulb one day after harvest.

GENERAL OBSERVATIONS

The 'Siberia' variety takes about 90 days to harvest in Ecuador, which is similar to the gladiolus variety 'Advance.' The 'Siberia' variety grows all year; however, growth is best during longer day lengths (i.e. 12–16 hours). The Siberia variety tolerates high temperatures well without burning.

The foliage is upright standing and usually produces one to two stems per Jumbo size corm (1.75 inches in diameter and larger). The variety can maintain up to six to seven flowers in open bloom simultaneously in a vase of water and can be harvested with one flower showing color. The variety is an excellent opener after transport in that the stems may be cut tight, shipped dry for a week, and still bloom well afterwards. The variety is also a slow opener.

The 'Siberia' variety has good resistance to attack by Fusarium fungi and foliar diseases. The variety does not emit a fragrance.

Compared to the T-200 parent variety, the 'Siberia' variety is 25 cm taller, has a larger bloom size that is about 2 cm wider in diameter, can hold one to two more blooms open, and is about two weeks slower to harvest. Disease resistance is similar to that of the 'T-200' variety, which is very good.

Compared to the Applicant's 'White Knight' variety (pending U.S. patent application Ser. No. 09/918,660), a sister variety, the 'Siberia' variety takes two weeks longer to harvest, has a head length that is about 8 cm shorter, has a bloom diameter that is about 1 cm larger, and produces stems that are about 4 to 6 cm longer when grown from the same size bulbs. Moreover, the bulb color of the 'Siberia' variety is Yellow Group 13B, whereas the bulb color for the 'White Knight' variety is a Yellow Orange Group 14A.

I claim:

1. A new and distinct gladiolus variety of plant named 'Siberia', as shown and described herein.

* * * * *